(12) United States Patent
Hwang et al.

(10) Patent No.: US 7,220,249 B2
(45) Date of Patent: May 22, 2007

(54) HINGED NEEDLE SHIELD ASSEMBLY HAVING NEEDLE CANNULA LOCK

(75) Inventors: Charles G Hwang, Ridgewood, NJ (US); C. Mark Newby, Tuxedo, NY (US)

(73) Assignee: Becton, Dickinson and Company, Franklin Lakes, NJ (US)

( * ) Notice: Subject to any disclaimer, the term of this patent is extended or adjusted under 35 U.S.C. 154(b) by 295 days.

(21) Appl. No.: 10/479,811

(22) PCT Filed: May 29, 2002

(86) PCT No.: PCT/US02/16800

§ 371 (c)(1),
(2), (4) Date: Dec. 5, 2003

(87) PCT Pub. No.: WO02/098481

PCT Pub. Date: Dec. 12, 2002

(65) Prior Publication Data

US 2004/0215154 A1    Oct. 28, 2004

(51) Int. Cl.
*A61M 5/00* (2006.01)
(52) U.S. Cl. ..................................... 604/263
(58) Field of Classification Search ............... 604/192, 604/198, 197, 164.08, 162, 263
See application file for complete search history.

(56) References Cited

U.S. PATENT DOCUMENTS

| | | |
|---|---|---|
| 1,779,451 A | 10/1930 | Sponsel |
| 2,004,050 A | 6/1935 | Kerk |
| 2,700,385 A | 1/1955 | Ortiz |
| 2,836,942 A | 6/1958 | Miskel |
| 2,854,976 A | 10/1958 | Heydrick |
| 2,953,243 A | 9/1960 | Roehr |
| 3,021,942 A | 2/1962 | Hamilton |
| 3,073,307 A | 1/1963 | Stevene |
| 3,074,542 A | 1/1963 | Myerson et al. |
| 3,255,873 A | 6/1966 | Speelman |
| 3,294,231 A | 12/1966 | Vanderbeck |
| 3,323,523 A | 6/1967 | Scislowicz et al. |
| 3,329,146 A | 7/1967 | Waldman, Jr. |
| 3,333,682 A | 8/1967 | Burke |
| 3,367,488 A | 2/1968 | Hamilton |
| 3,485,239 A | 12/1969 | Vanderbeck |
| 3,537,452 A | 11/1970 | Wilks |
| 3,610,240 A | 10/1971 | Harautuneian |
| 3,658,061 A | 4/1972 | Hall |
| 3,828,775 A | 8/1974 | Armel |

(Continued)

FOREIGN PATENT DOCUMENTS

GB    1233302    5/1971

(Continued)

*Primary Examiner*—Sharon E. Kennedy
(74) *Attorney, Agent, or Firm*—Jeanne P. Lukasavage

(57) ABSTRACT

A needle shield assembly and method of manufacturing a needle shield are provided. The needle shield assembly includes a needle hub having a needle cannula extending therefrom. A needle shield base is pivotably coupled to the needle hub. A locking assembly including a needle engagement member is coupled to the needle shield base. One or both of the needle shield base and the locking assembly include a cavity for receiving the needle cannula. The needle shield is manufactured by providing a needle shield base and a separate locking assembly including a needle engagement member, and connecting the locking assembly to the distal end portion of the needle shield base.

21 Claims, 19 Drawing Sheets

U.S. PATENT DOCUMENTS

| | | |
|---|---|---|
| 3,890,971 A | 6/1975 | Leeson et al. |
| 3,904,033 A | 9/1975 | Haerr |
| 3,934,722 A | 1/1976 | Goldberg |
| 3,968,876 A | 7/1976 | Brookfield |
| 4,113,090 A | 9/1978 | Carstens |
| 4,139,009 A | 2/1979 | Alvarez |
| 4,175,008 A | 11/1979 | White |
| 4,300,678 A | 11/1981 | Gyure et al. |
| RE31,086 E | 11/1982 | Johnson, Jr. et al. |
| 4,375,849 A | 3/1983 | Hanifl |
| 4,430,082 A | 2/1984 | Schwabacher |
| 4,592,744 A | 6/1986 | Jagger et al. |
| 4,634,428 A | 1/1987 | Cuu |
| 4,643,722 A | 2/1987 | Smith, Jr. |
| 4,659,330 A | 4/1987 | Nelson et al. |
| 4,664,249 A | 5/1987 | Gherardi |
| 4,664,259 A | 5/1987 | Landis |
| 4,664,654 A | 5/1987 | Strauss |
| 4,671,408 A | 6/1987 | Raines et al. |
| 4,681,567 A | 7/1987 | Masters et al. |
| 4,695,274 A | 9/1987 | Fox |
| 4,702,738 A | 10/1987 | Spencer |
| 4,723,943 A | 2/1988 | Spencer |
| 4,728,320 A | 3/1988 | Chen |
| 4,728,321 A | 3/1988 | Chen |
| 4,731,059 A | 3/1988 | Wanderer et al. |
| 4,735,311 A | 4/1988 | Lowe et al. |
| 4,735,618 A | 4/1988 | Hagen |
| 4,737,144 A | 4/1988 | Choksi |
| 4,738,663 A | 4/1988 | Bogan |
| 4,743,233 A | 5/1988 | Schneider |
| 4,746,008 A | 5/1988 | Heverly et al. |
| 4,747,836 A * | 5/1988 | Luther ........................ 604/198 |
| 4,747,837 A | 5/1988 | Hauck |
| 4,772,272 A | 9/1988 | McFarland |
| 4,778,453 A | 10/1988 | Lopez |
| 4,781,697 A | 11/1988 | Slaughter |
| 4,782,841 A | 11/1988 | Lopez |
| 4,790,828 A | 12/1988 | Dombrowski et al. |
| 4,793,484 A | 12/1988 | Schoettle |
| 4,795,432 A | 1/1989 | Karczmer |
| 4,795,443 A | 1/1989 | Permenter et al. |
| 4,801,295 A | 1/1989 | Spencer |
| 4,804,372 A | 2/1989 | Laico et al. |
| 4,813,426 A | 3/1989 | Haber et al. |
| 4,816,022 A | 3/1989 | Poncy |
| 4,816,024 A | 3/1989 | Sitar et al. |
| 4,819,659 A | 4/1989 | Sitar |
| 4,820,277 A | 4/1989 | Norelli |
| 4,826,490 A | 5/1989 | Byrne et al. |
| 4,826,491 A | 5/1989 | Schramm |
| 4,838,871 A | 6/1989 | Luther |
| 4,842,587 A | 6/1989 | Poncy |
| 4,846,796 A | 7/1989 | Carrell et al. |
| 4,850,968 A | 7/1989 | Romano |
| 4,850,976 A | 7/1989 | Heinrich et al. |
| 4,850,977 A | 7/1989 | Bayless |
| 4,850,978 A | 7/1989 | Dudar et al. |
| 4,850,994 A | 7/1989 | Zerbst et al. |
| 4,850,996 A | 7/1989 | Cree |
| 4,858,607 A | 8/1989 | Jordan et al. |
| 4,863,434 A | 9/1989 | Bayless |
| 4,863,435 A | 9/1989 | Sturman et al. |
| 4,863,436 A | 9/1989 | Glick |
| 4,867,746 A | 9/1989 | Dufresne |
| 4,872,552 A | 10/1989 | Unger |
| 4,874,383 A | 10/1989 | McNaughton |
| 4,874,384 A | 10/1989 | Nunez |
| 4,883,469 A | 11/1989 | Glazier |
| 4,886,503 A | 12/1989 | Miller |
| 4,888,001 A | 12/1989 | Schoenberg |
| 4,892,107 A | 1/1990 | Haber |
| 4,892,521 A | 1/1990 | Laico et al. |
| 4,900,309 A | 2/1990 | Netherton et al. |
| 4,909,791 A | 3/1990 | Norelli |
| 4,909,792 A | 3/1990 | Norelli |
| 4,921,096 A | 5/1990 | McFarlane |
| 4,927,018 A | 5/1990 | Yang et al. |
| 4,944,397 A | 7/1990 | Miller |
| 4,966,591 A | 10/1990 | Yuen |
| 4,976,699 A | 12/1990 | Gold |
| 4,982,842 A | 1/1991 | Hollister |
| 5,011,475 A | 4/1991 | Olson |
| 5,011,479 A | 4/1991 | Le et al. |
| 5,055,102 A | 10/1991 | Sitnik |
| 5,078,693 A | 1/1992 | Shine |
| 5,116,325 A | 5/1992 | Paterson |
| 5,135,509 A | 8/1992 | Olliffe |
| 5,139,489 A | 8/1992 | Hollister |
| 5,151,089 A | 9/1992 | Kirk, III et al. |
| 5,154,285 A | 10/1992 | Hollister |
| 5,188,611 A | 2/1993 | Orgain |
| 5,197,954 A | 3/1993 | Cameron |
| 5,207,653 A | 5/1993 | Janjua et al. |
| 5,232,454 A | 8/1993 | Hollister |
| 5,232,455 A | 8/1993 | Hollister |
| 5,242,417 A | 9/1993 | Paudler |
| 5,277,311 A | 1/1994 | Hollister |
| 5,312,369 A | 5/1994 | Arcusin et al. |
| 5,401,251 A | 3/1995 | Hui |
| 5,405,332 A | 4/1995 | Opalek |
| 5,423,765 A | 6/1995 | Hollister |
| 5,462,534 A | 10/1995 | Debreczeni |
| 5,485,854 A | 1/1996 | Hollister |
| 5,486,163 A | 1/1996 | Haynes |
| 5,490,841 A | 2/1996 | Landis |
| 5,509,907 A * | 4/1996 | Bevilacqua ................. 604/263 |
| 5,533,984 A | 7/1996 | Parmigiani |
| 5,584,816 A | 12/1996 | Gyure et al. |
| 5,599,313 A | 2/1997 | Gyure et al. |
| 5,599,318 A | 2/1997 | Sweeney et al. |
| 5,603,699 A | 2/1997 | Shine |
| 5,632,732 A * | 5/1997 | Szabo et al. ................. 604/192 |
| 5,643,219 A | 7/1997 | Burns |
| 5,662,617 A | 9/1997 | Odell et al. |
| 5,665,075 A | 9/1997 | Gyure et al. |
| 5,669,889 A | 9/1997 | Gyure et al. |
| 5,693,022 A | 12/1997 | Haynes |
| 5,702,369 A | 12/1997 | Mercereau |
| 5,733,265 A | 3/1998 | Bachman et al. |
| 5,807,351 A * | 9/1998 | Kashmer .................... 604/263 |
| 5,836,920 A | 11/1998 | Robertson |
| 5,885,249 A | 3/1999 | Irisawa |
| 5,913,846 A | 6/1999 | Szabo |
| 5,993,426 A | 11/1999 | Hollister |
| 6,077,253 A | 6/2000 | Cosme |
| 6,080,137 A | 6/2000 | Pike |
| 6,120,482 A | 9/2000 | Szabo |
| 6,139,533 A | 10/2000 | Xia et al. |
| RE37,110 E | 3/2001 | Hollister |
| RE37,252 E | 7/2001 | Hollister |
| 6,319,232 B1 | 11/2001 | Kashmer |
| 6,328,713 B1 | 12/2001 | Hollister |
| 6,334,857 B1 | 1/2002 | Hollister et al. |
| 6,699,217 B2 | 3/2004 | Bennett et al. |
| 2004/0215154 A1 | 10/2004 | Hwang et al. |
| 2005/0054986 A1 | 3/2005 | Simpson et al. |
| 2005/0065481 A1 | 3/2005 | Hauri et al. |
| 2005/0065482 A1 | 3/2005 | Hauri et al. |

FOREIGN PATENT DOCUMENTS

| | | |
|---|---|---|
| GB | 2239604 | 7/1991 |
| GB | 2239607 | 7/1991 |

| | | | | | | |
|---|---|---|---|---|---|---|
| GB | | 2240273 | 7/1991 | WO | WO 91/09638 | 7/1991 |
| GB | | 2240477 | 8/1991 | WO | WO 91/09639 | 7/1991 |
| WO | WO 87/07162 | | 12/1987 | WO | WO 93/16745 | 9/1993 |
| WO | WO 90/01348 | | 2/1990 | | | |
| WO | WO 91/09637 | | 7/1991 | * cited by examiner | | |

HINGED NEEDLE SHIELD ASSEMBLY HAVING NEEDLE CANNULA LOCK

FIELD OF THE INVENTION

The field of the invention relates to needle shield assemblies for medical devices such as hypodermic needles, and to methods for manufacturing such assemblies.

BACKGROUND OF THE INVENTION

Accidental needle sticks from used hypodermic needles can transmit disease. Accordingly, various types of needle shields have been designed to reduce the possibility of accidental needle sticks.

A needle shield that is hinged near the base of the needle has the advantage of allowing one handed needle reshielding. A number of prior art needle shield assemblies include hinged needle shields.

Various means have been provided for locking a hinged needle shield in the closed, needle protecting position. Deflectable members have been provided in the needle shield for engaging the needle upon shielding and preventing subsequent unshielding of the needle. Such members trap the needle within the needle shield. Locking has also been accomplished by locking engagement of the needle shield with the needle support structure.

SUMMARY OF THE INVENTION

A needle shield assembly of the present invention includes a needle cannula that is secured to the distal end of a needle hub having a proximal end, a distal end. The hub may be provided with a proximal end for connecting to a medical device such as a syringe. A needle shield base is pivotably coupled to the needle hub. A discrete locking assembly having one or more locking members for engaging the needle cannula is provided. The locking assembly is coupled to the distal end portion of the needle shield base such that the one or more locking members are lockingly engageable with the needle cannula. At least one of the needle shield base and locking assembly include a cavity for receiving at least part of the needle cannula.

In a first embodiment of the invention, the needle shield base has a first cavity and the locking assembly includes a cap defining a second cavity. The cap is secured to a part of the needle shield base such that the first and second cavities are contiguous and the one or more locking members thereof are engageable with the shaft of the needle cannula.

In a second embodiment of the invention, the needle shield base and locking assembly are constructed such that they can be coupled at a plurality of locations. The positioning of the locking assembly with respect to the needle shield allows the locking member(s) of the locking assembly to be positioned to engage the needle cannula when the shield is pivoted to the closed position. Relatively long or short needle cannulas can be accommodated.

A third embodiment of the invention includes a needle shield base including means for coupling to a locking assembly. The locking assembly can be chosen to engage a needle of selected length.

A method of manufacturing needle shield is also provided. The method includes the steps of providing a needle shield base including a connector for pivotably connecting it to a medical device, providing a locking assembly having a needle engagement member, and coupling the needle shield base to the locking assembly.

DETAILED DESCRIPTION OF THE INVENTION

Figure 1:
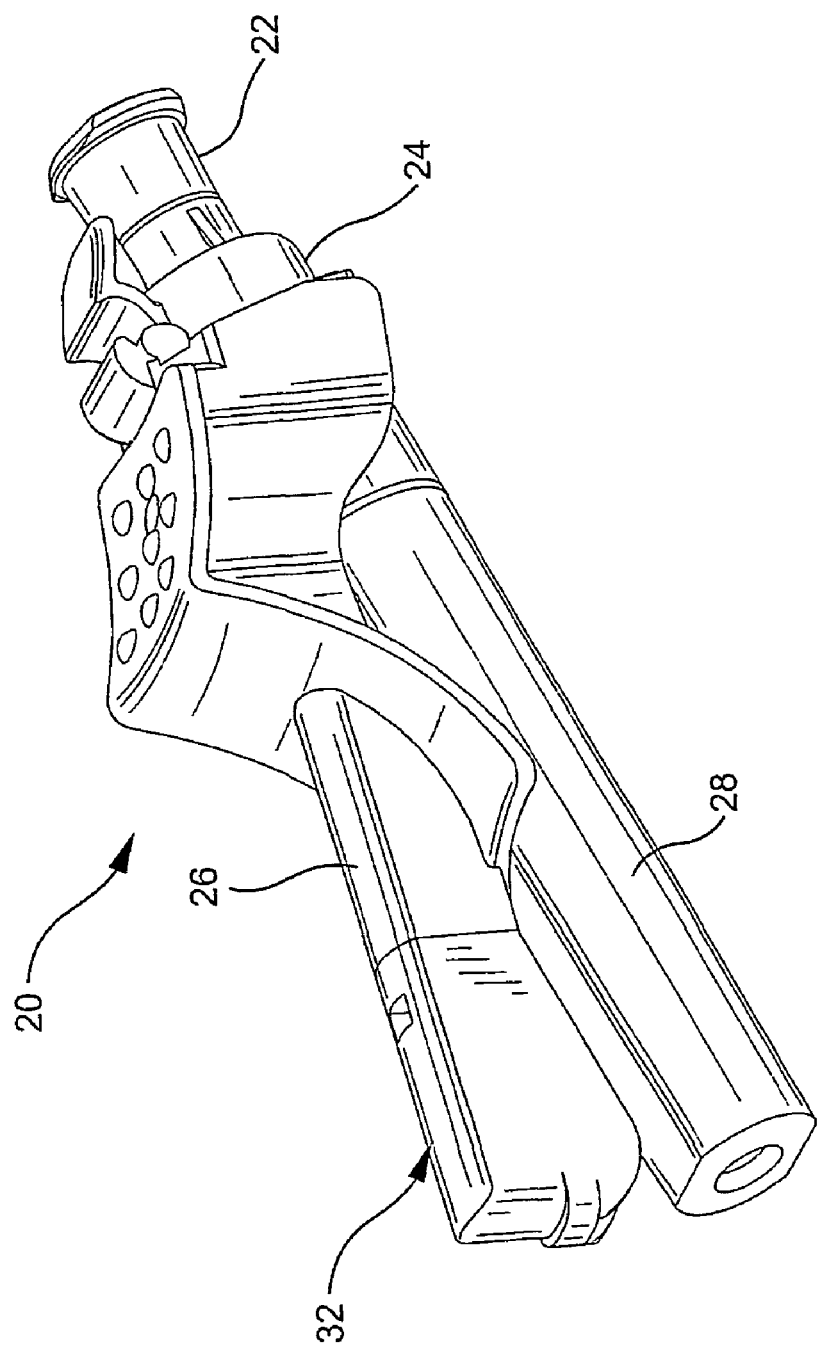
FIG. 1 is a top perspective view showing a needle shield assembly in accordance with a first embodiment of the invention.

There is shown in the drawings and described below in detail preferred embodiments of the invention with the understanding that the present disclosure is to be considered as exemplary of the principles of the invention and is not intended to limit the invention to the embodiments illustrated.

Figure 2:
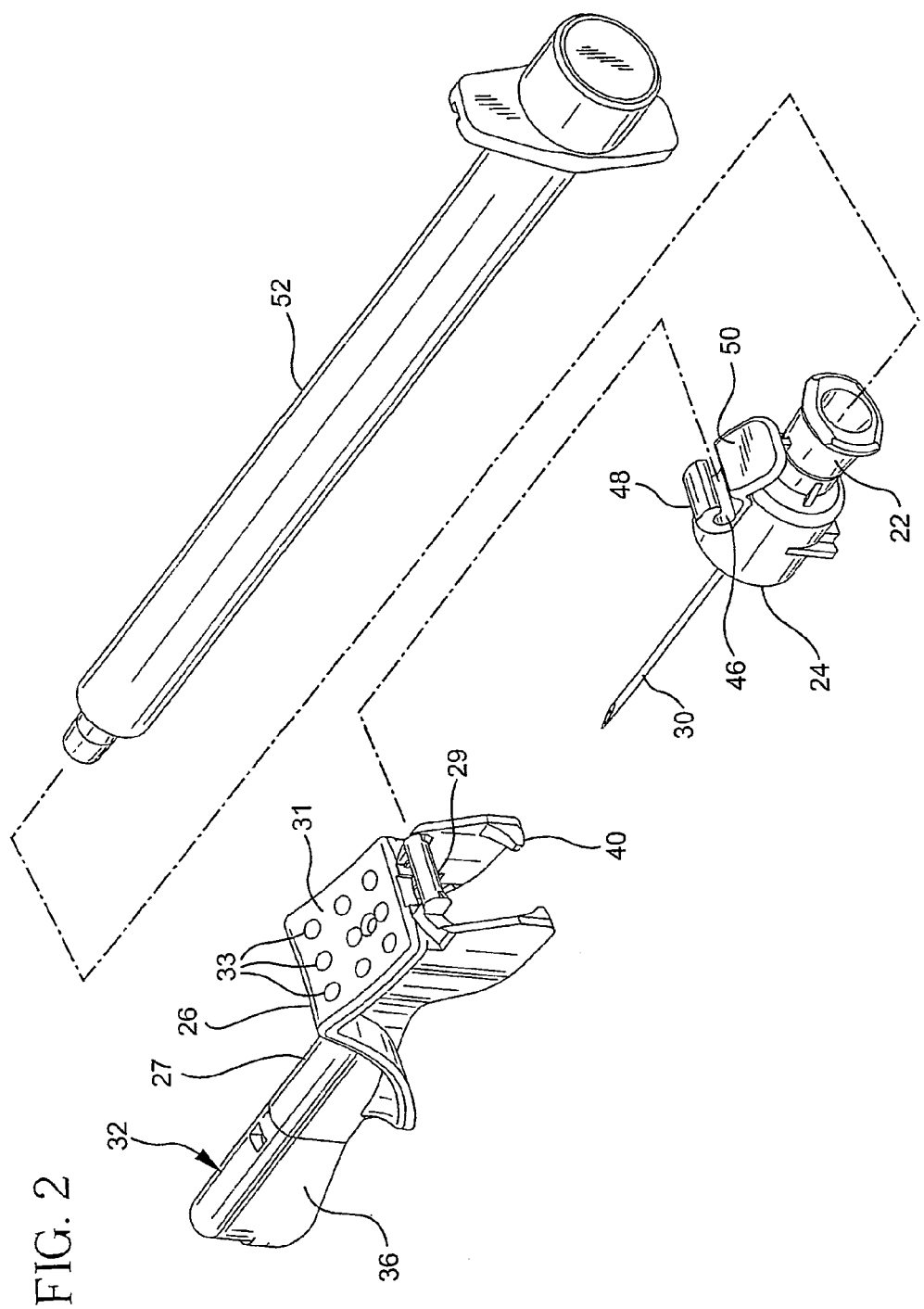
FIG. 2 is an exploded, top perspective view showing parts of the needle shield assembly in combination with a medical fluid delivery device.

Referring to FIGS. 1 and 2, a needle shield assembly 20 is provided that includes a needle hub 22, a base member 24 connected to or integral with the needle hub, a needle shield base 26, and a needle cover 28. The needle shield base includes a proximal end portion that can be connected to the needle hub or base member, and a relatively distal end portion 27 that includes an elongate cavity for enveloping at least part of a needle cannula 30. The proximal end portion of the needle shield base 26 includes an integral hinge pin 29 and a curved upper surface 31. The upper surface 31 is designed for engagement by a user's finger in order to rotate the needle shield about the hinge pin. Projections 33 may be provided on the curved upper surface.

Needle cannulas are available in many different lengths and gauges as they maybe used for different purposes. If the needle shield is to be locked in the protective position by the engagement of a locking member engaging the needle shaft, it is important that the locking member (or members) be positioned properly. The needle shield base 26 of the invention, being either molded to a desired length or cut to length following the molding process, allows it to be customized for a particular needle cannula length.

Figure 3:
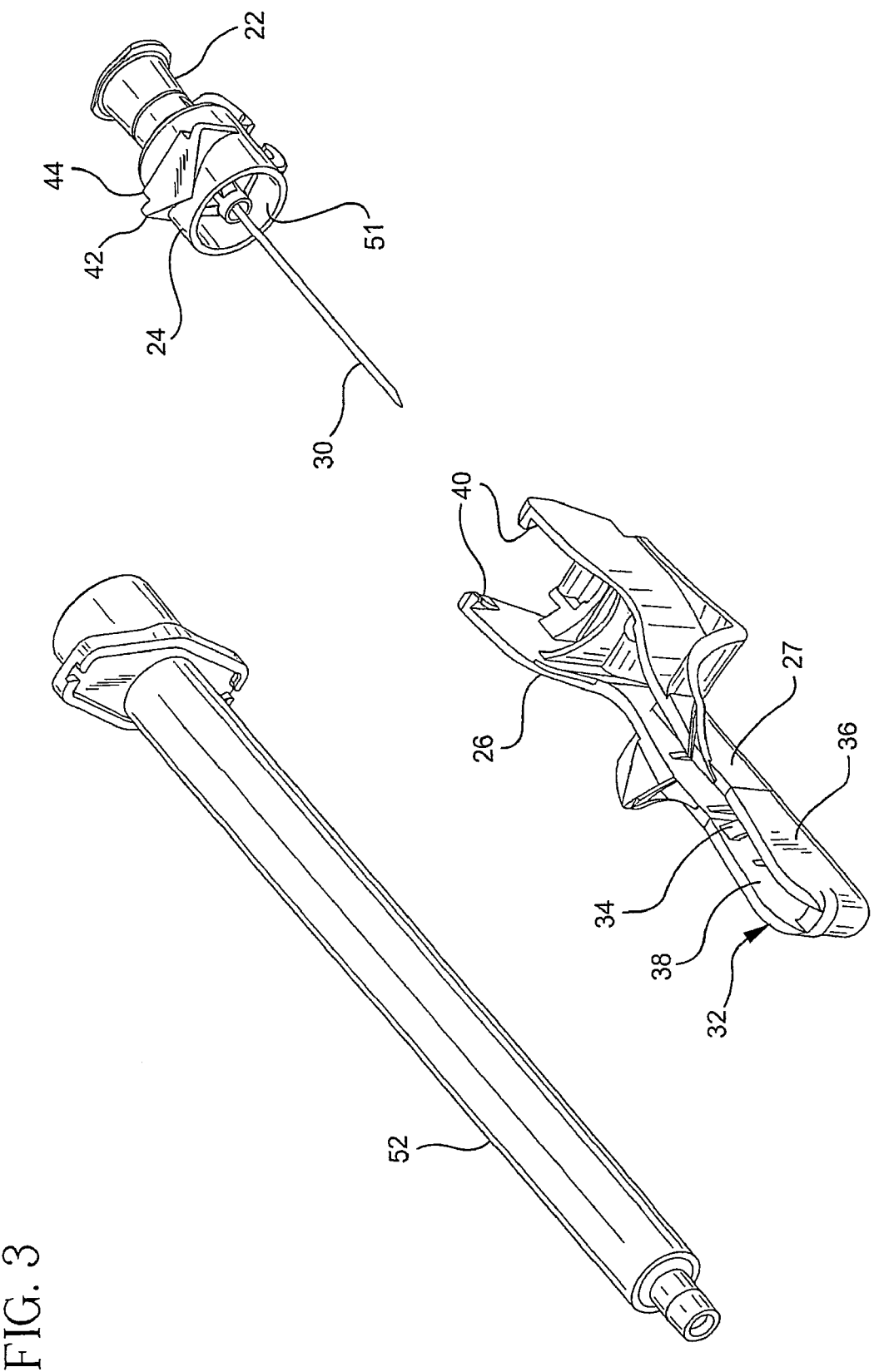
FIG. 3 is an exploded, bottom perspective view of the needle shield assembly and fluid delivery device of FIG. 2.
Figure 9:
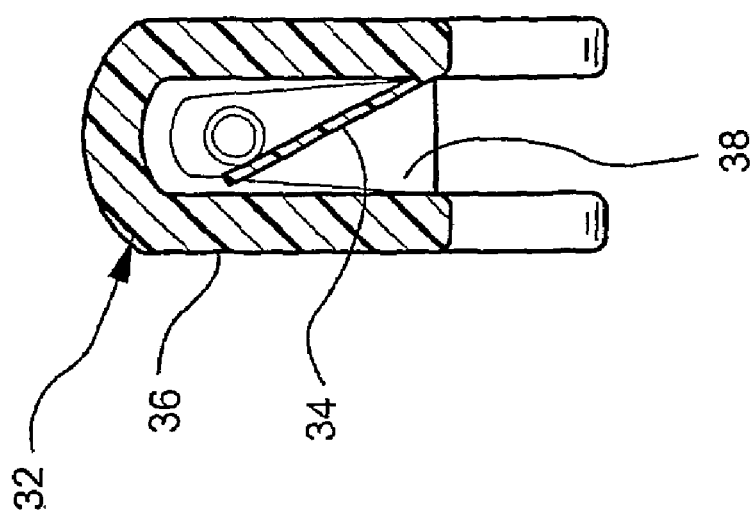
FIG. 9 is a cross-sectional view of a locking assembly for the needle shield taken along line 9—9 of FIG. 8.
Figure 10:
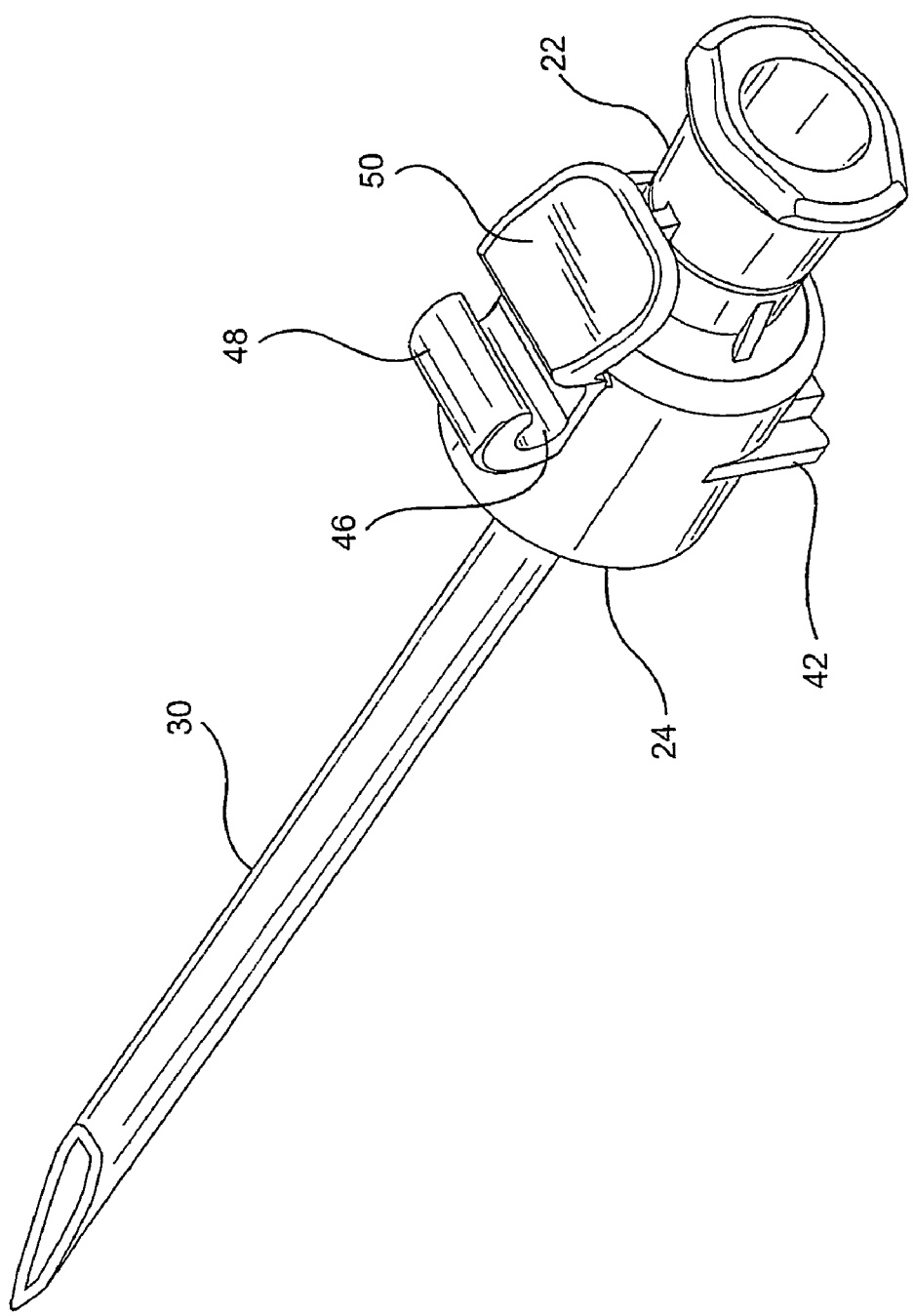
FIG. 10 is a top perspective view of a needle assembly to which the needle shield can be mounted.
Figure 11:
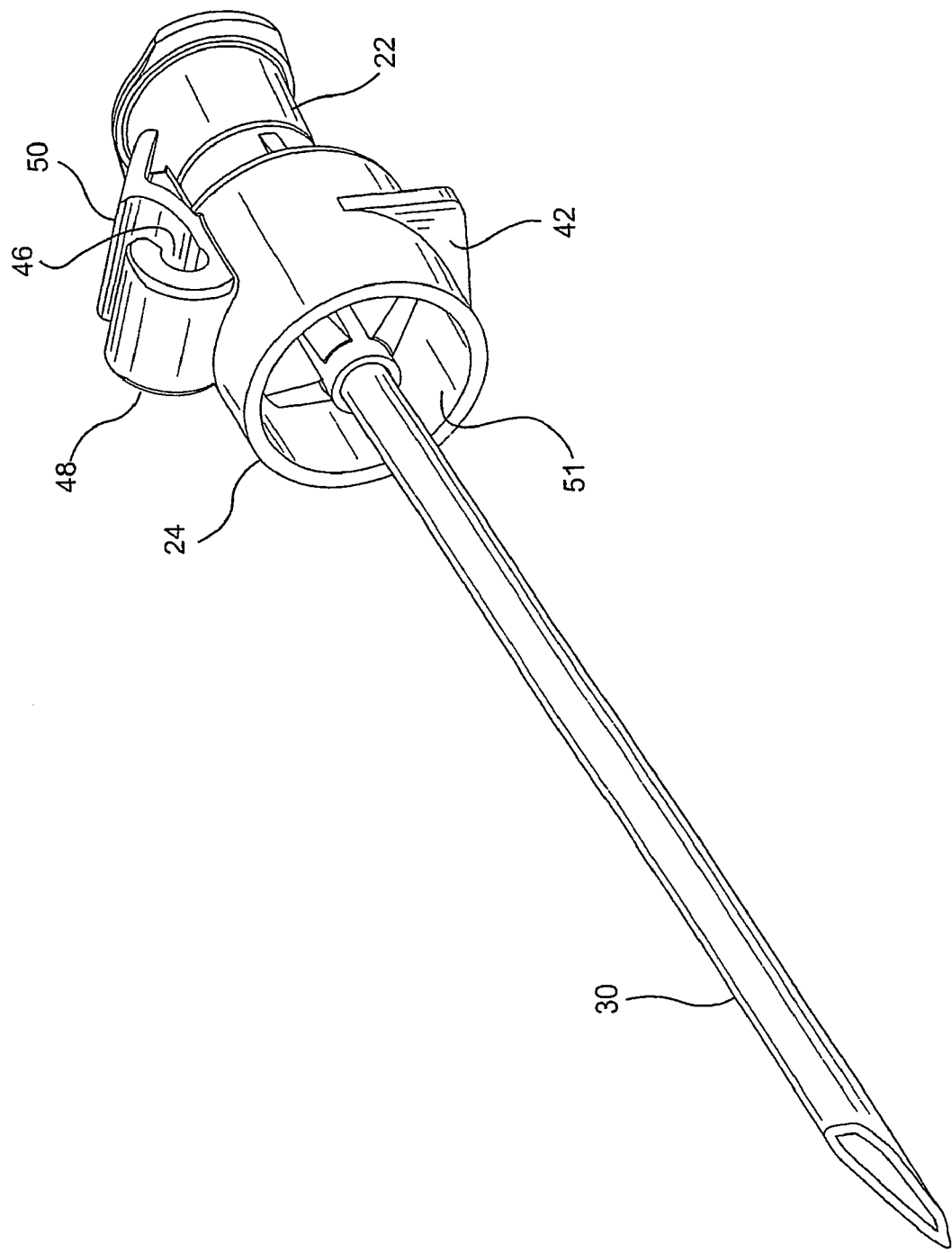
FIG. 11 is a top perspective view thereof taken from a different point.
Figure 12:
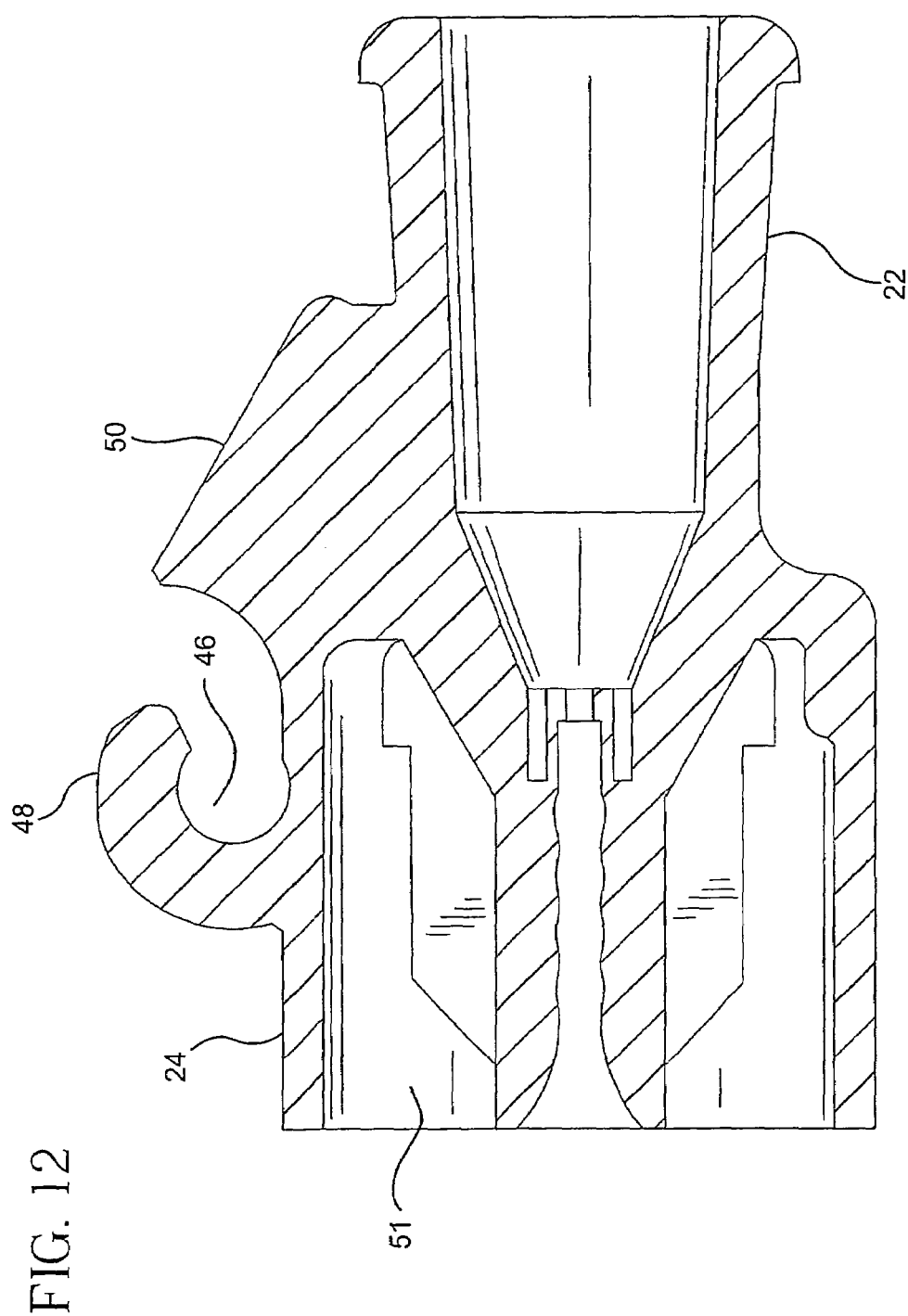
FIG. 12 is a cross-sectional view of the needle hub and base member.
Figure 14:
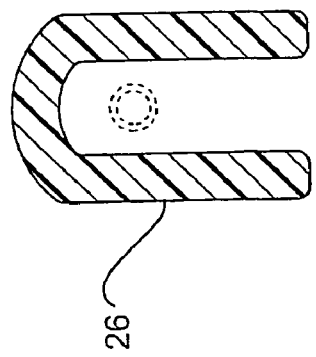
FIG. 14 is a cross-sectional view thereof taken along line 14—14 of FIG. 13.

A discrete locking assembly 32 including a locking member 34 is provided for attachment to the distal end portion of the needle shield base 26. The locking assembly 32 is comprised of a cap 36 that has a generally U-shaped cross section and that defines a cavity 38, as shown in FIG. 9. The cavity 38 of the cap is axially aligned with the elongate cavity of the needle shield base 26 when the cap is coupled to the needle shield base, as shown in FIG. 3. It will be understood that the relative lengths of the distal end portion of the needle shield base and the cap 36 may be different from those shown in the drawings, and that either can be longer than the other or the same length as the other. While there is no locking member in the needle shield base of the preferred embodiment shown in the drawings, both the cap and needle shield base can include one or more locking members for engaging the needle cannula shaft. Locking member 34 is shown as integral with the cap 36, and having a base connected to one of the opposing side walls of the cap near the opening of cavity 38. The locking member 34 is deflectable towards the side wall to which it is connected as the cap and connected needle shield base are urged over a needle cannula.

The cap 36 can be secured to the distal end of the needle shield base by an adhesive, by welding or by mechanical connectors. The distal end portion of the needle shield base is preferably open-ended while the cap preferably has a closed or partially closed distal end that is intended to shield the pointed end of the needle cannula. The proximal end portion of the cap is open-ended. The needle shield/cap assembly can be manufactured in several different ways. Both the needle shield base and cap can be injection molded from a suitable plastic material such as polypropylene, polyethylene or combinations thereof. The needle shield base can be molded to the desired length, or made large enough to accommodate a range of needle cannula lengths and then cut, if necessary, to the desired length. The cap is then secured to the needle shield.

While the distal end portion of the needle shield base 26 preferably defines an elongate cavity, such a cavity is not critical, and the cap can define the only cavity of the device. The proximal end portion of the needle shield base may include projections or tabs 40 for lockingly engaging the needle hub 22 or base member 24.

The base member 24 of the preferred embodiment includes a projection 42 having notches 44 for receiving the locking projections 40 at the proximal end of the needle shield base 26, as shown in FIG. 3. The base member further includes a channel 46 having arcuate walls for receiving the hinge pin 29 on the needle shield base. As shown in FIGS. 2 and 10–12, the channel 46 is positioned between a C-shaped projection 48 and a ramp 50. A cylindrical recess 51 in the base member 24 is provided for receiving the proximal end of the needle cover 28.

The needle hub includes a proximal end adapted for connection to a medical device such as a syringe 52. Various types of connectors are known and considered to be within the purview of the present invention. When secured to the medical device, fluid communication is established between the needle cannula 30 and the inner chamber 54 of the device.

Figure 4:
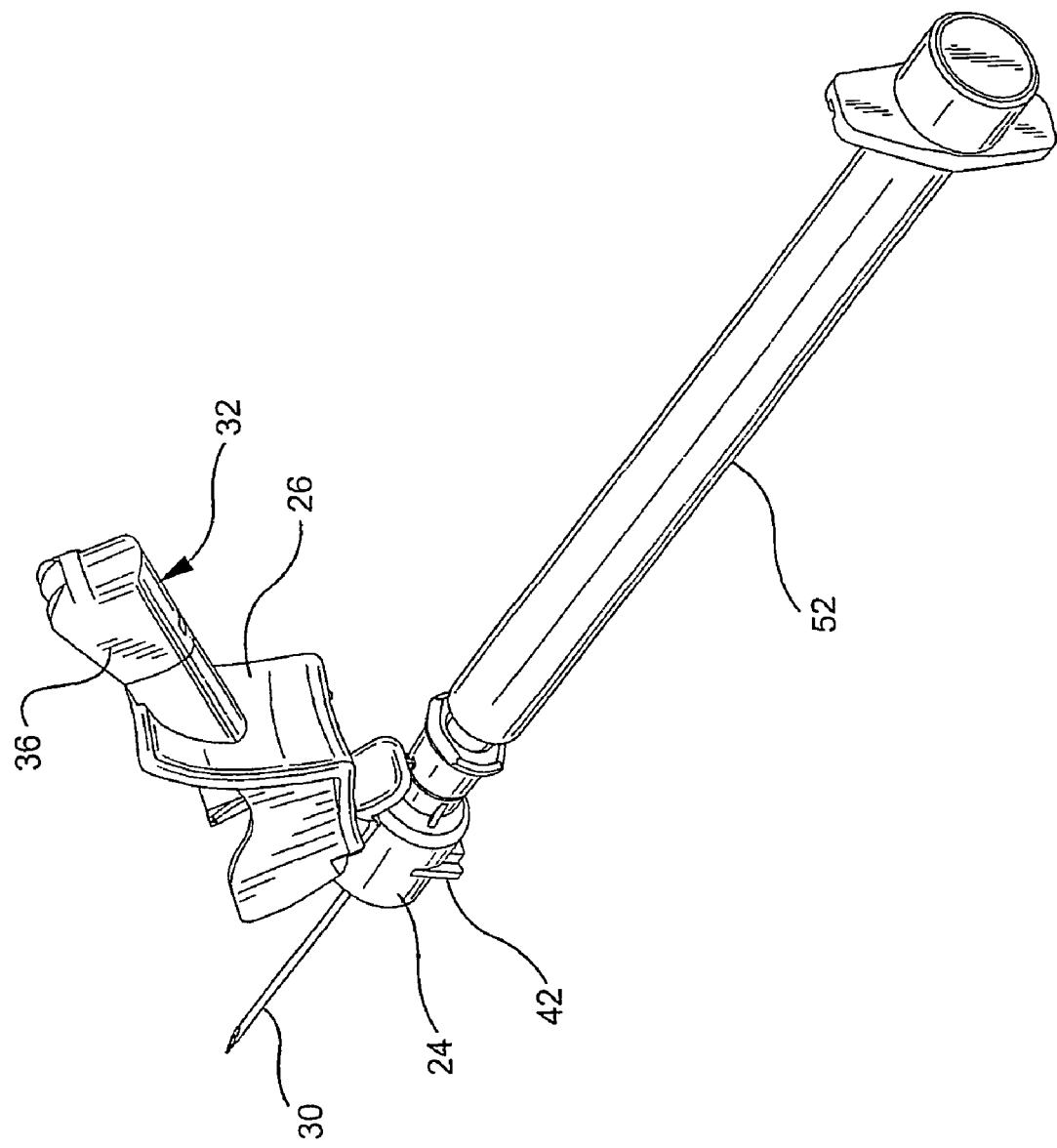
FIG. 4 is a perspective view showing the needle shield assembly mounted to a medical fluid delivery device, the needle cannula of the assembly being exposed.
Figure 5:
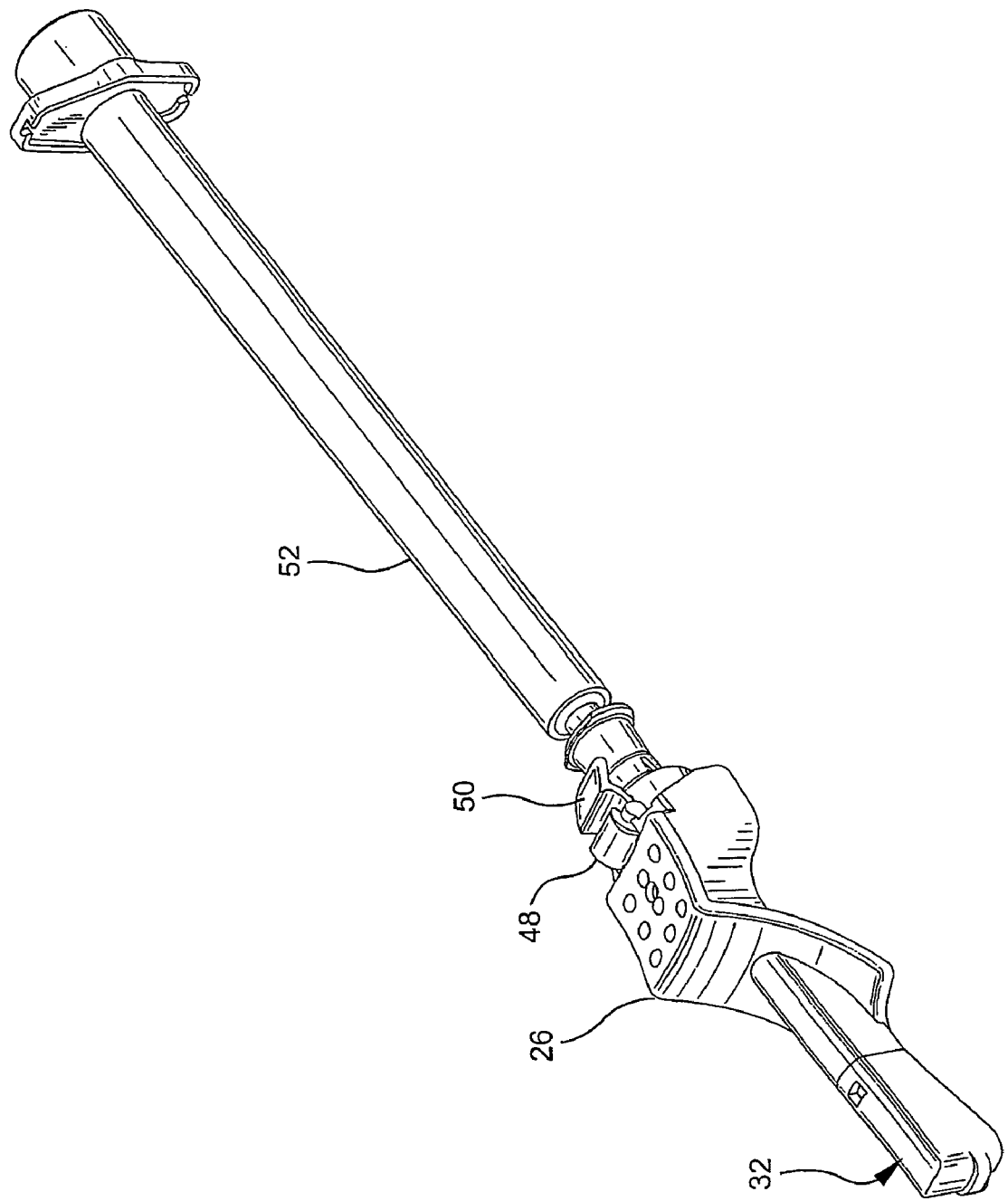
FIG. 5 is a perspective view thereof showing the needle shield in a protective position covering the needle cannula.
Figure 6:
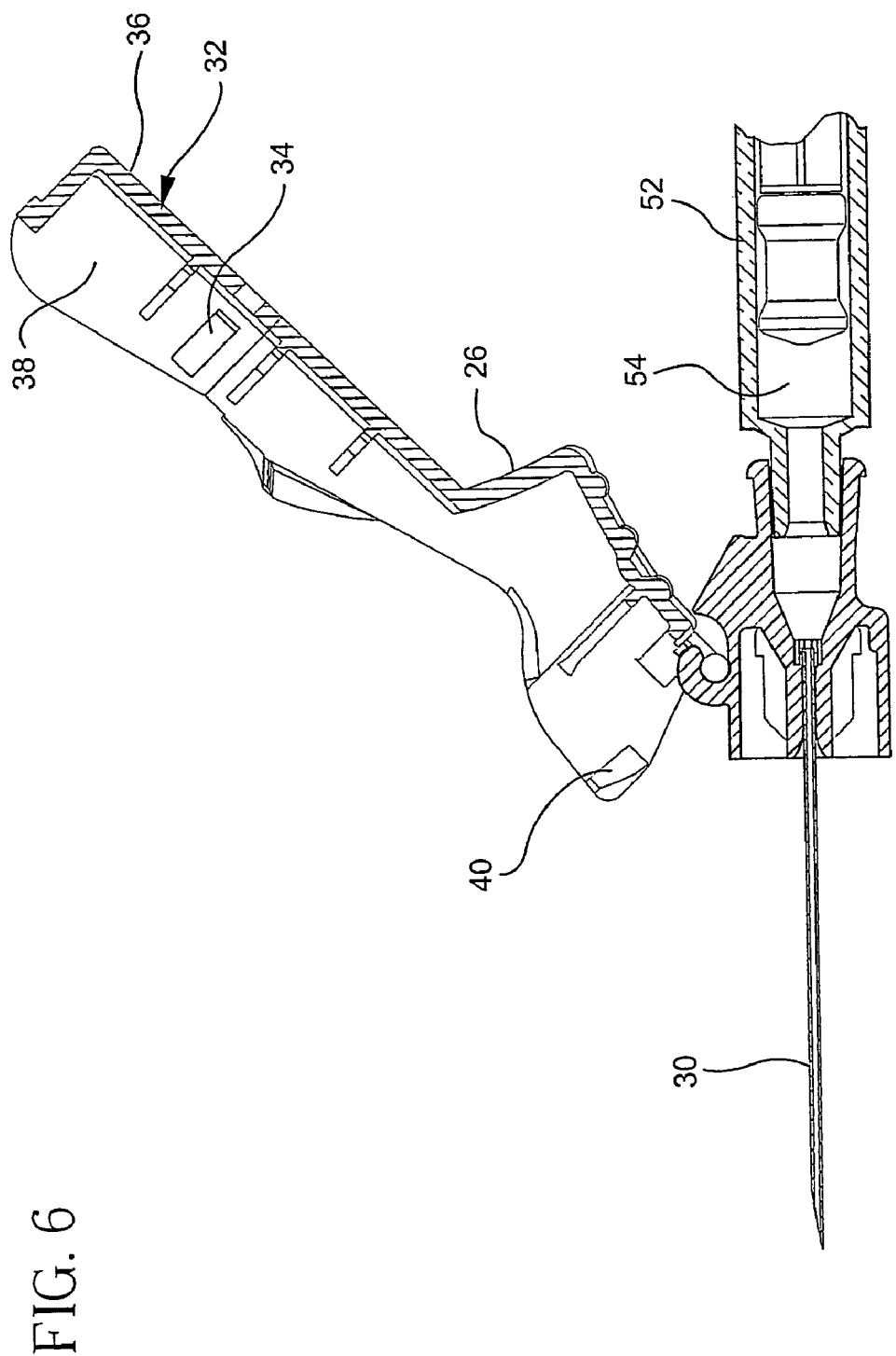
FIG. 6 is a cross-sectional view of the needle shield assembly and the medical fluid delivery device showing the needle shield in a first position.
Figure 7:
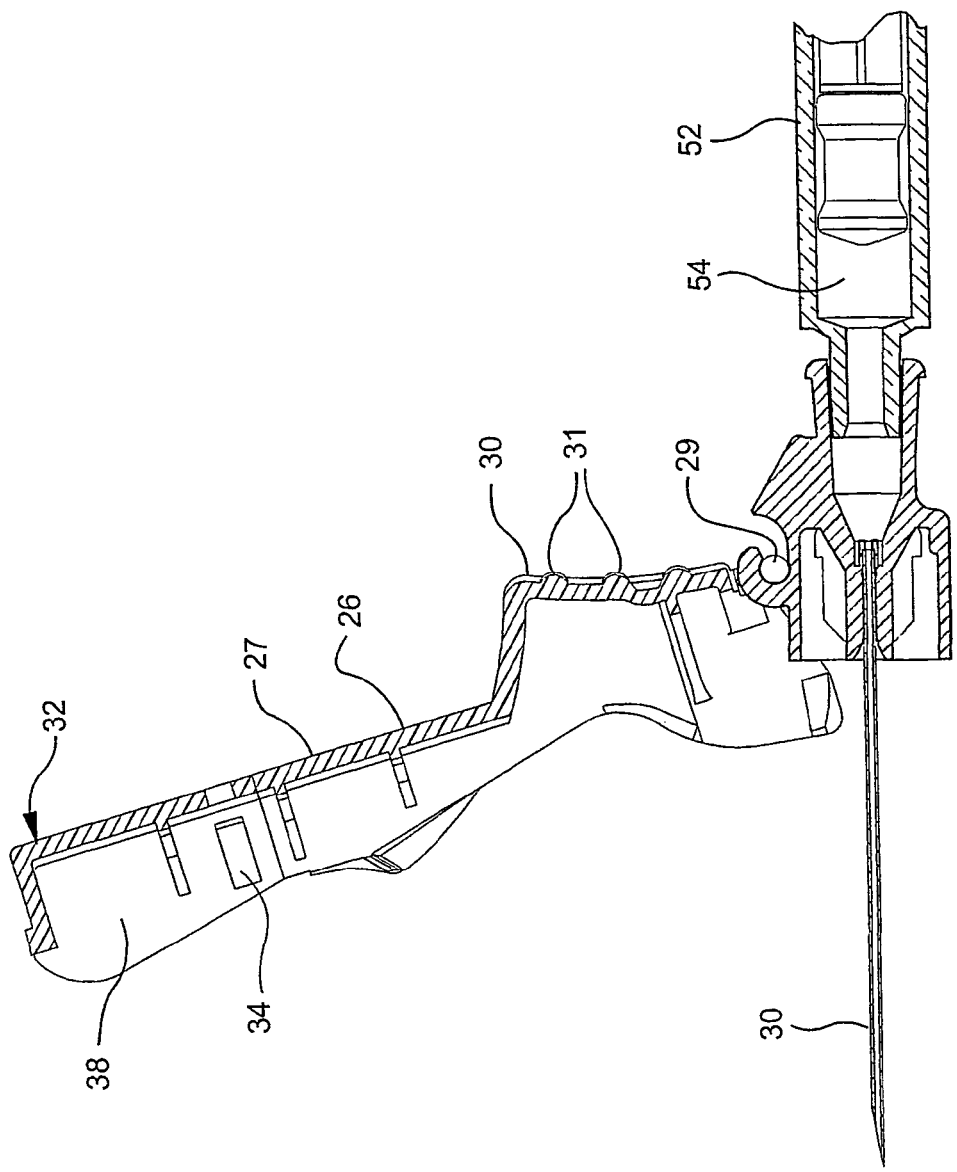
FIG. 7 is a cross-sectional view thereof showing the needle shield partially rotated towards a protective position.
Figure 8:
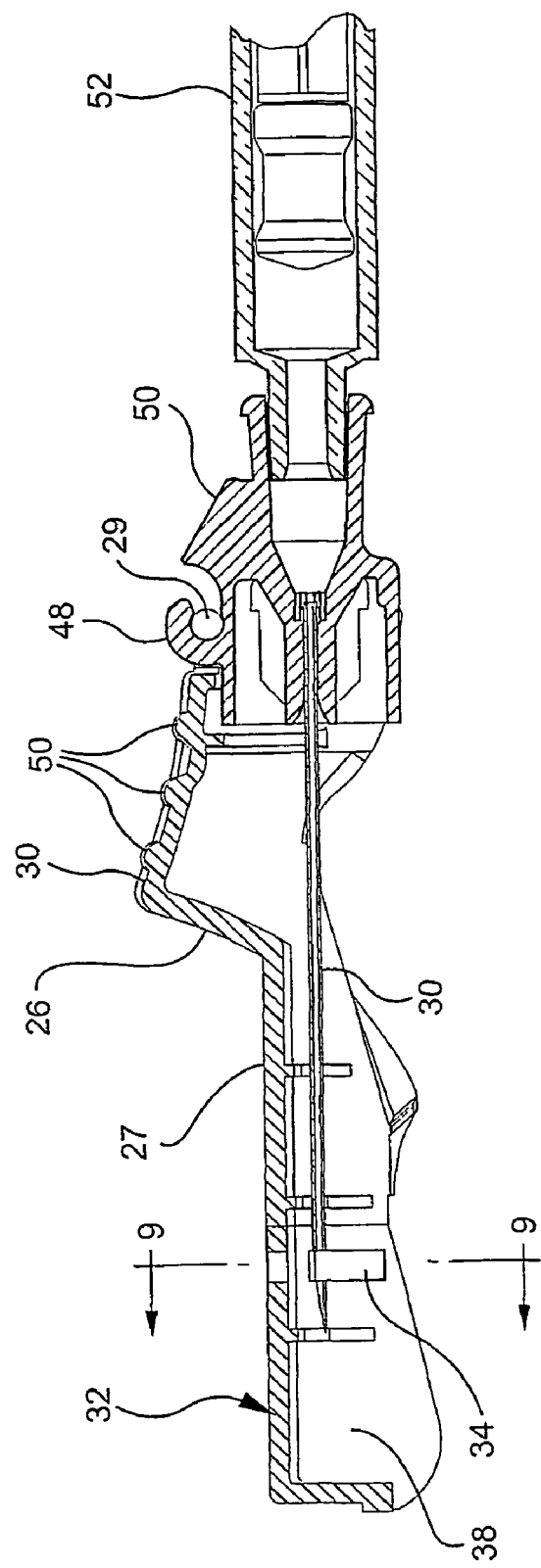
FIG. 8 is a cross-sectional view thereof showing the needle shield in a protective position covering the needle cannula.

The needle shield base 26 and associated locking assembly 32, which together comprise a needle shield, can be pivoted about the hinge pin 29 between the open position shown in FIGS. 4 and 6 and the closed position shown in FIGS. 5 and 8. The locking member 34 is displaced towards a side wall of the cap 36 as the needle cannula 30 enters the cavity 38. Once the needle cannula has moved sufficiently into the cavity, the locking member 34 springs back to its original position, thereby entrapping the needle cannula as shown in FIG. 9.

Figure 13:
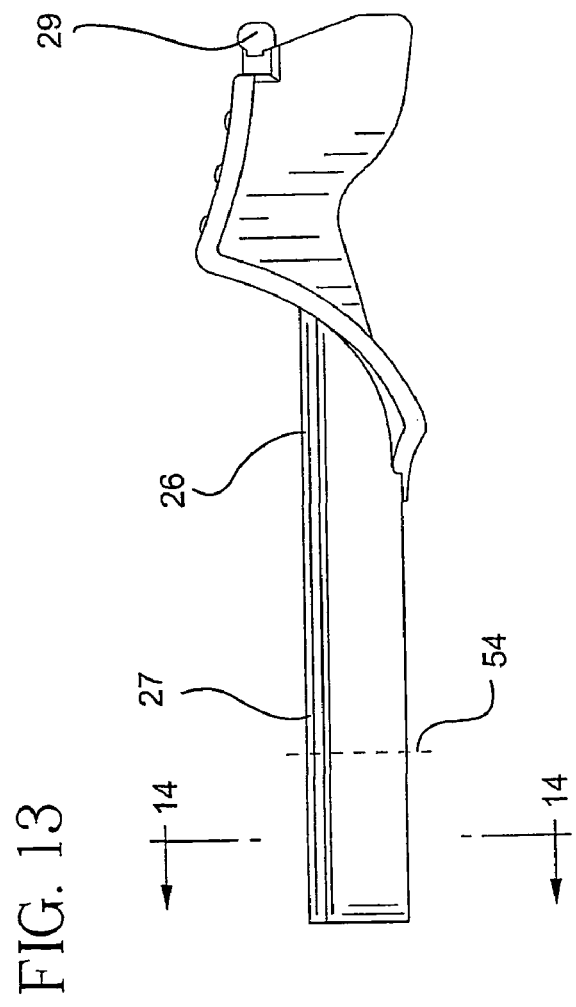
FIG. 13 is a side elevation view of a needle shield showing a partition line.
Figure 15:
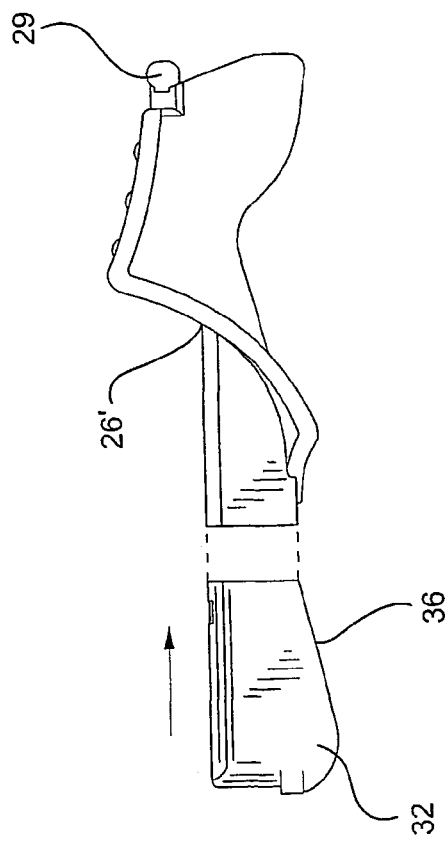
FIG. 15 is a side elevation view of a needle shield cut to a first selected length.
Figure 16:
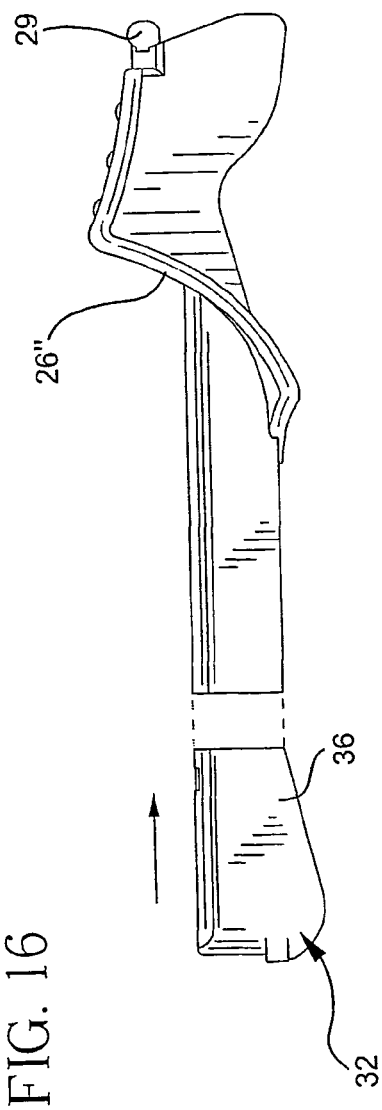
FIG. 16 is a side elevation view of a needle shield cut to a second selected length.

FIG. 13 shows a needle shield base 26 having a distal end portion 27 manufactured to a selected length. The locking assembly 32 may be secured to the shield base as manufactured if the locking member 34 will be engageable with the needle cannula 30 with which it is used. If the needle shield base is to be used to protect a shorter needle cannula, it can be severed at a selected point, as indicated by way of example at line 54. FIGS. 15 and 16 illustrate needle shield bases 26', 26" severed to relatively short and long lengths, respectively, prior to securement of the locking assembly 32.

Figure 17:
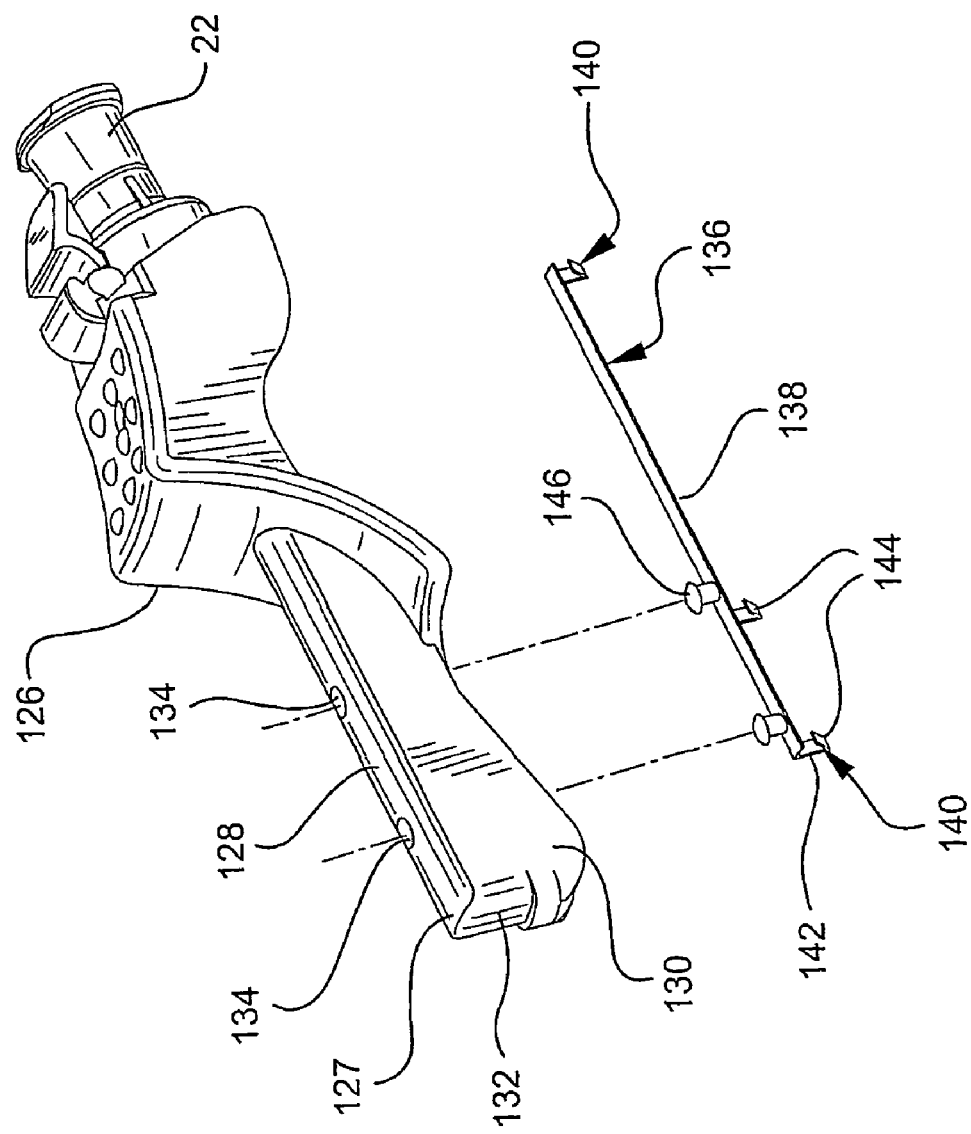
FIG. 17 is an exploded, perspective view of an alternative embodiment of the needle shield assembly.

A second embodiment of the invention is shown in FIG. 17. In this embodiment, the needle shield base 126 is manufactured to a selected length that can preferably accommodate a plurality of lengths of needle cannulas. The distal end portion 127 of the needle shield base includes a top wall 128, opposing side walls 130 and an end wall 132 that define an elongate cavity. A pair of openings 134 extend through the top wall 128. The same numerals are employed to designate similar elements found in the shield of the previous embodiment.

A locking assembly 136 is provided for coupling to the needle shield base. The locking assembly includes an elongate rail 138 having one or more locking members 140. Each locking member includes a downwardly extending wall 142 and a projection 144 preferably extending upwardly at an acute angle with respect to the wall 142. The locking members are resilient and can be deflected by the shaft of a needle cannula. They will also spring back to their original positions once a needle cannula is entrapped. A pair of projections 146 extend upwardly from the rail 138. Each projection has an enlarged end portion that can be forced through one of the openings 134 in the top wall of the needle shield base, thereby providing a locking engagement with the shield. Other types of mechanical locking elements can be employed to couple the shield base 126 and the locking assembly 136. These elements can also be coupled by an adhesive heat staking or other suitable means.

Figure 18:
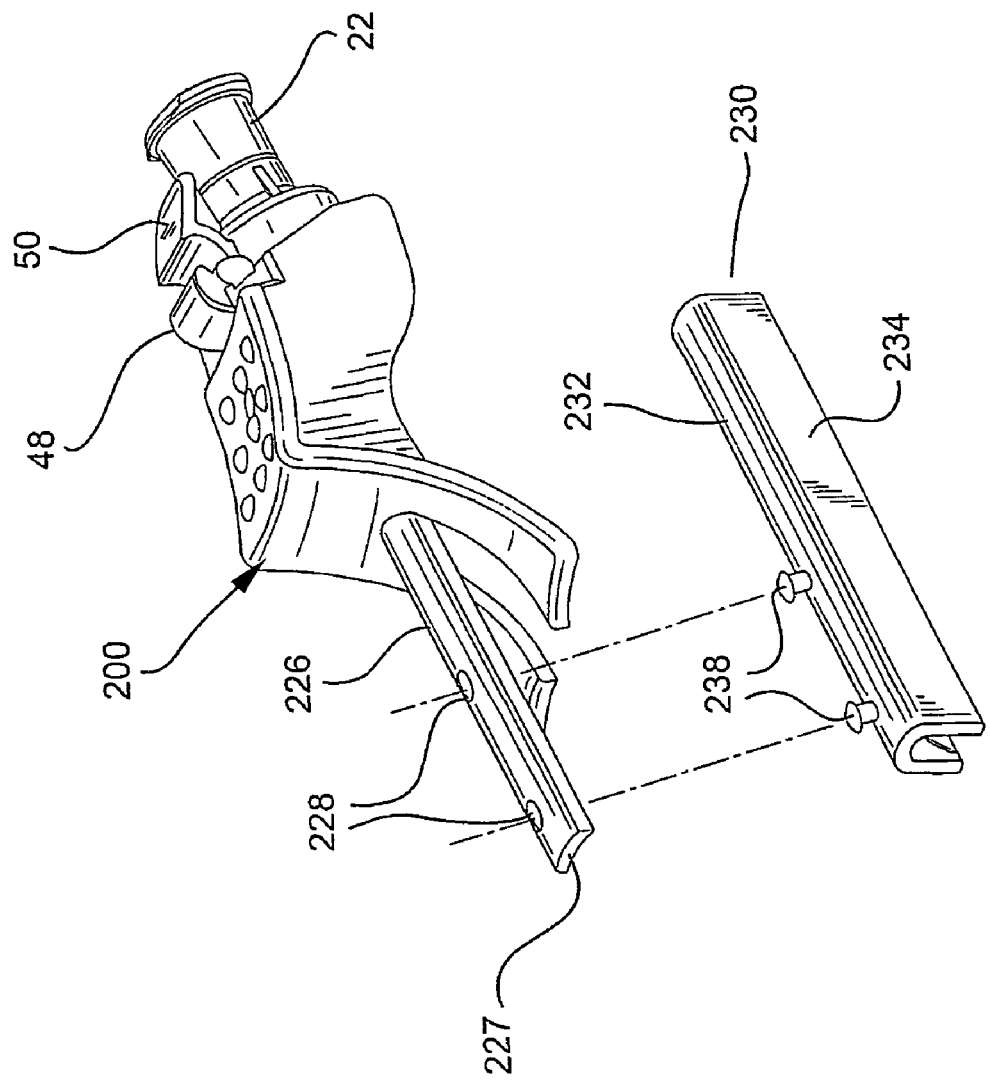
FIG. 18 is an exploded, perspective view of a second alternative embodiment of the needle shield assembly.
Figure 20:
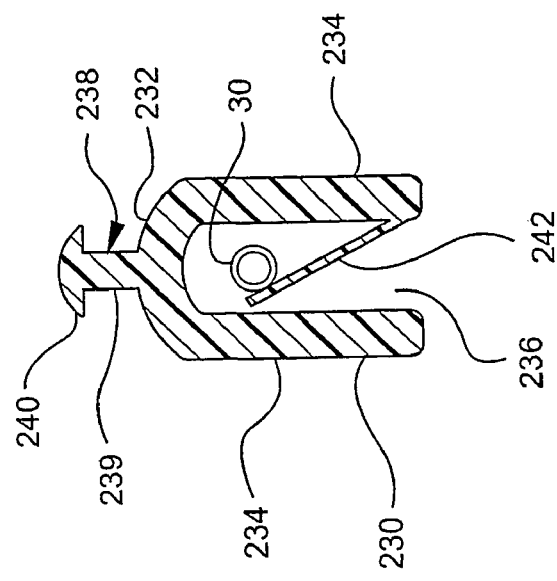
FIG. 20 is a cross-sectional view thereof taken along line 20—20 of FIG. 19.
Figure 19:
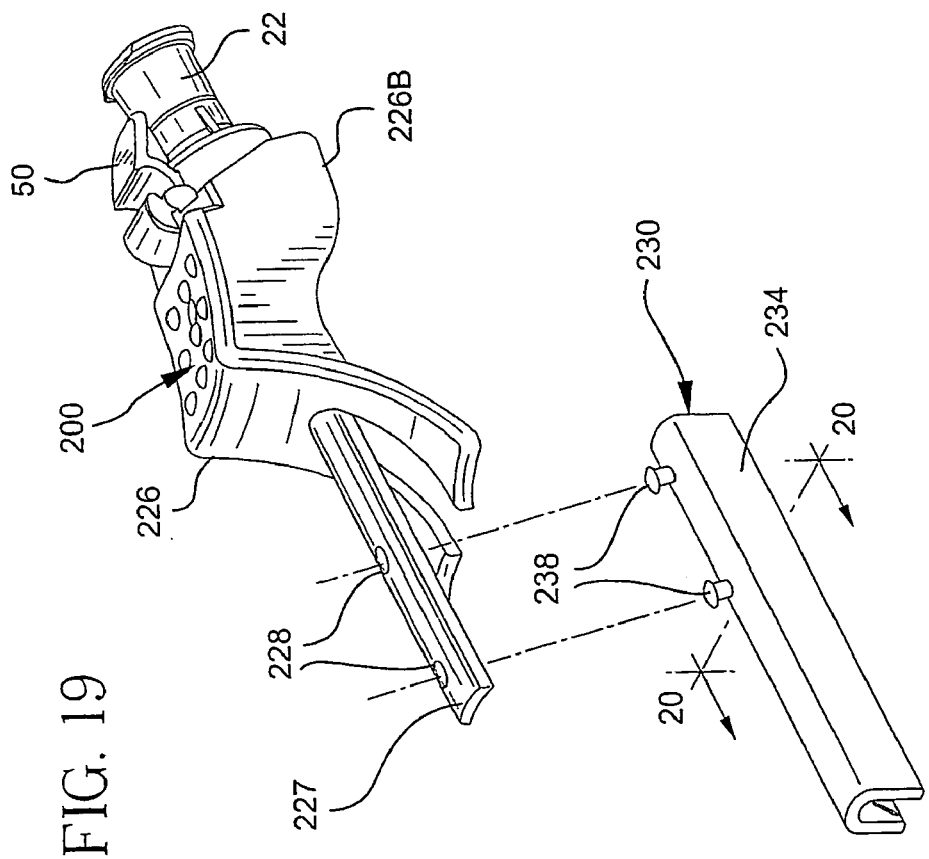
FIG. 19 is an exploded, perspective view thereof showing the locking assembly mounted to the needle shield in a different orientation from that shown in FIG. 13.

FIGS. 18–20 show a third embodiment of the invention. In this embodiment, the needle shield assembly 200 includes a needle shield base 226 having a proximal end portion similar to those described above. The same numerals are accordingly used to designate similar parts. The distal end portion 227 thereof is in the form of an elongate rail. A pair of holes 228 extend through the rail. A locking assembly 230 is provided for coupling to the distal end portion of the needle shield base. It includes a top wall 232 and a pair of opposing side walls 234 that define an elongate channel 236. A pair of projections 238 extend from the top wall 232 of the locking assembly. Each projection includes a shaft 239 having an enlarged head 240 that may be tapered to facilitate entrance into the holes 228 in the distal end portion of 227 of the needle shield. These elements are best shown in FIG. 20. One or more projections 242, each preferably integral with one of the side walls 234. The projection is connected to the side wall 234 near the channel opening, and is deflectable towards the side wall about its connection. The locking assembly may be secured to the needle shield base in either of two orientations as shown in FIGS. 18 and 19. Needles of different lengths can accordingly be accommodated with the same needle shield base and locking assembly. As discussed above, different types of locking arrangements can be used to couple the needle shield base and locking assembly.

Figure 21:
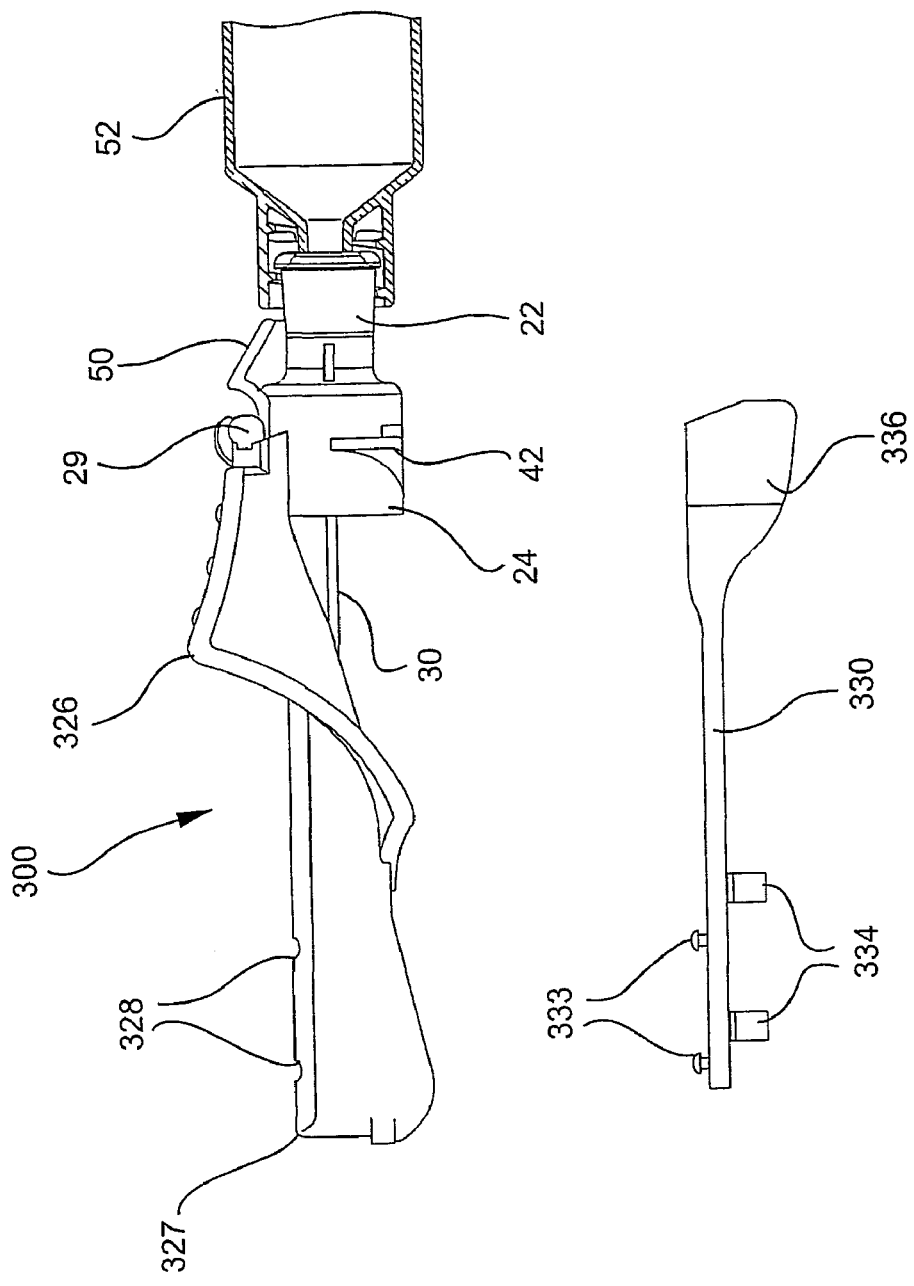
FIG. 21 is a partially exploded side elevation view of a third alternative embodiment of the needle shield assembly secured to a medical device.

A fourth embodiment of the invention is shown in FIG. 21. A needle shield assembly 300 is comprised of a needle shield base 326 similar to those of the first two embodiments. The same numerals are accordingly employed to designate common elements of the needle shield base, hub and base member found in these embodiments. The distal end portion 327 of the needle shield base 326 includes a pair of holes 328 extending through the top wall thereof and opening into the elongate needle shield channel. A locking assembly 330 is provided for connection to the needle shield base. The locking assembly 330 is comprised of an elongate rail 332 having a pair of projections 333 extending upwardly from the top surface of the rail and a pair of locking members 334 extending downwardly from the rail. Each projection 333 includes a shaft having an enlarged head that is sized to snap through holes 328 in distal end portion 327 of needle shield base 326, thereby permanently coupling the needle shield and locking assembly. Locking members 334 are formed as generally V-shaped structures beneath the rail 332. They are deflectable by a needle cannula shaft as the needle shield (comprising the needle shield base 326 and locking assembly 330) is closed, and spring back to their original positions once the needle shield is fully closed. The needle cannula shaft is thereby entrapped within the V-shaped portions of the locking members 334. It will be appreciated that a greater or lesser number of locking members can be employed.

Figure 22:
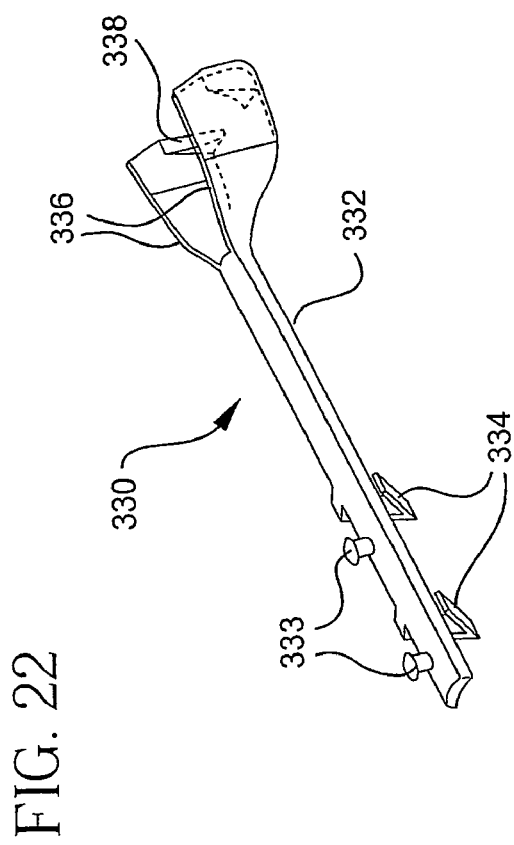
FIG. 22 is a top perspective view of the locking assembly thereof.
Figure 23:
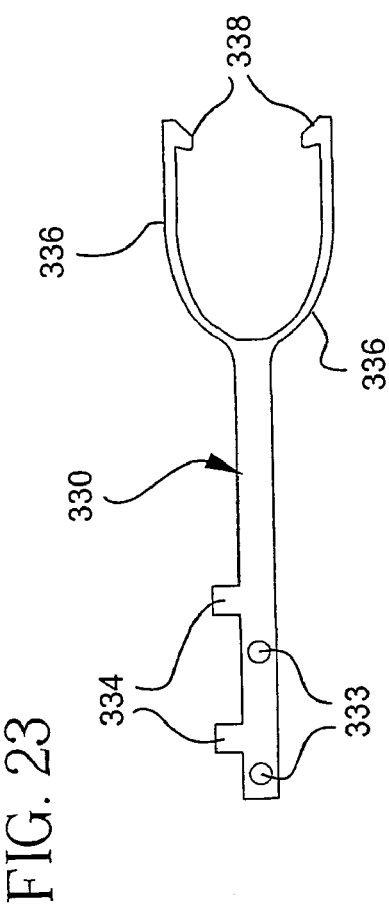
FIG. 23 is a top plan view thereof.

The proximal end portion of the locking assembly 330 is bifurcated as shown in FIGS. 21–22 to accommodate the base member 24. Each opposing wall 336 thereof includes an inwardly extending projection 338. When the locking assembly is coupled to the needle shield base, the projections are capable of engaging the projection 42 on the base member 24, thereby locking the needle shield in the closed, needle protecting position.

What is claimed is:

1. A needle shield assembly comprising:
    a needle hub having a proximal end and a distal end;
    a needle cannula secured to the distal end of said hub;
    a needle shield base having a proximal end portion and a distal end portion, said proximal end portion being pivotably connected to said needle hub;
    a separate locking assembly coupled to said distal end portion of said needle shield base, said separate locking assembly comprising a cap having a first cavity and including a needle engagement member extending into said first cavity, wherein said first cavity receives at least a portion of said needle cannula.

2. The needle shield assembly of claim 1 wherein said distal end portion of said needle shield base includes a shield portion having a second cavity, said first and second cavities being contiguous.

3. The needle shield assembly of claim 2 wherein said shield portion of said needle shield base has an open distal end and said cap has an open proximal end joined to said open distal end of said shield portion.

4. The needle shield assembly of claim 2 wherein said cap has a closed distal end.

5. The needle shield assembly of claim 1 wherein said distal end portion of said needle shield base includes an elongate rail and said locking assembly includes a body defining an elongate cavity, said body being connected to said elongate rail.

6. A needle shield assembly comprising:
    a needle hub having a proximal end and a distal end;
    a needle cannula secured to the distal end of said hub;
    a needle shield base having a proximal end portion and a distal end portion, said proximal end portion being pivotably connected to said needle hub;
    a separate locking assembly coupled to said distal end portion of said needle shield base, said separated locking assembly including a needle engagement member; and
    at least one of said needle shield base and said locking assembly including a cavity for receiving at least a portion of said needle cannula, wherein said needle shield base and said separate locking assembly include complementary locking members connecting said needle shield base and said separate locking assembly.

7. The needle shield assembly of claim 6 wherein said locking assembly includes an elongate rail, said needle engagement member being connected to said rail.

8. The needle shield assembly of claim 6 wherein said needle shield base includes an elongate cavity, said rail being positioned within said elongate cavity.

9. The needle shield assembly of claim 6 wherein said distal end portion of said needle shield base includes an elongate rail and said locking assembly includes a body defining an elongate cavity, said body being connected to said elongate rail.

10. The needle shield assembly of claim 6 wherein said needle shield base includes an elongate cavity, and said locking assembly is positioned at least partially in said elongate cavity.

11. The needle shield assembly of claim 10 wherein said locking assembly includes means for locking said needle shield base and said locking assembly to said needle hub.

12. A method of manufacturing a needle shield, comprising:
    providing a needle shield base having a proximal end portion and a distal end portion, said proximal end portion including a connector for pivotably connecting said needle shield base to a medical device;
    providing a locking assembly including a needle engagement member; and
    connecting said locking assembly to said distal end portion of said needle shield base.

13. The method of claim 12 wherein said locking assembly comprises a cap including a first cavity, wherein said needle engagement member extends into said first cavity.

14. The method of claim 13 wherein said distal end portion of said needle shield base includes a shield portion having a second cavity, positioned so that upon connecting said cap to said shield portion, said first and second cavities are contiguous.

15. The method of claim 14 wherein said shield portion has an open distal end and said cap has an open proximal end, including the step of connecting said open distal end of said shield portion with said open proximal end of said cap.

16. The method of claim 12 wherein said needle shield base and said locking assembly include complementary locking members, including the step of connecting said needle shield base and said locking assembly by coupling said complementary locking members.

17. The method of claim 16 wherein said locking assembly includes an elongate rail, said needle engagement member being connected to said rail.

18. The method of claim 17 wherein said needle shield base includes an elongate cavity, including the step of positioning said rail within said cavity.

19. The method of claim 16 wherein said distal end portion of said needle shield base includes an elongate rail and said locking assembly includes a body defining an elongate cavity, including the step of connecting said body of said locking assembly to said elongate rail.

20. The method of claim 12 wherein said distal end portion of said needle shield base includes an elongate rail and said locking assembly includes a body defining an elongate cavity, including the step of connecting said body of said locking assembly to said elongate rail.

21. The method of claim 12 wherein said needle shield base includes an elongate cavity, including the step of positioning said locking assembly at least partially within said elongate cavity.

* * * * *